US008180132B2

(12) United States Patent
Gorges et al.

(10) Patent No.: US 8,180,132 B2
(45) Date of Patent: May 15, 2012

(54) METHOD TO CORRECT THE REGISTRATION OF RADIOGRAPHY IMAGES

(75) Inventors: Sebastien Gorges, Paris (FR); Yves Lucien Trousset, Palaiseau (FR); Jeremie Pescatore, Le Chesnay (FR); Erwan Kerrien, Nancy (FR); Marie-Odile Berger, Maron (FR)

(73) Assignee: General Electric Company, Schenectady, NY (US)

( * ) Notice: Subject to any disclaimer, the term of this patent is extended or adjusted under 35 U.S.C. 154(b) by 963 days.

(21) Appl. No.: 12/170,465

(22) Filed: Jul. 10, 2008

(65) Prior Publication Data

US 2009/0022381 A1 Jan. 22, 2009

(51) Int. Cl.
*G06K 9/00* (2006.01)
(52) U.S. Cl. .................. 382/131; 382/294
(58) Field of Classification Search .......... 382/128–132, 382/285, 294, 295
See application file for complete search history.

(56) References Cited

U.S. PATENT DOCUMENTS

| 2005/0004454 A1 | 1/2005 | Mitschke et al. | 600/427 |
| 2006/0079759 A1 | 4/2006 | Vaillant et al. | 600/424 |
| 2007/0172033 A1 | 7/2007 | Gorges | 378/207 |
| 2007/0238947 A1 | 10/2007 | Pescatore et al. | 600/407 |

FOREIGN PATENT DOCUMENTS

| EP | A1081647 | 3/2001 |
| FR | 2797978 | 3/2001 |
| FR | 2802002 | 6/2001 |
| FR | 2879433 | 6/2006 |

OTHER PUBLICATIONS

Kerrien, Erwan; et al: "Machine Precision Assessment for 3D/2D Digital Substracted Angiography Images Registration" Proceedings of the Spie, Spie, Bellingham, VA, US, vol. 3338, Feb. 1998, pp. 39-49, XP000920613, ISSN: 0277-786X.
Baert, Shirley; et al: "Three-Dimensional Guide-Wire Reconstruction From Biplane Image Sequences for Integrated Display in 3-d Vasculature", IEEE Transaction on Medical Imaging, IEEE Service Center, Piscataway, NJ, US, vol. 22, No. 10, Oct. 2003, pp. 1252-1258, XP000920613, ISSN: 0278-0062.
Schmitt, Holger, et al., Reconstruction of blood propogation in three-dimensional rotational X-ray angiography (3D-RA), Computerized Medical Imaging and Graphics 29 (2005).

*Primary Examiner* — Courtney Thomas
(74) *Attorney, Agent, or Firm* — Global Patent Operation; Jonathan E. Thomas

(57) ABSTRACT

A system and method for correcting the registration of a 3D image and a 2D image acquired with medical imaging systems is disclosed. The system and method determines acquisition geometry of the imaging system by calculating an initial projection matrix associated with the 2D image. The system performs a projection of the 3D image using the initial projection matrix resulting in a 2D projection of the 3D image. The system registers the 2D projection of the 3D image and the 2D image. A new projection matrix is determined based on the registration of the 2D image and the 2D projection of the 3D image. The 3D image is then registered with the 2D image using the new projection matrix. An associated medical imaging system is disclosed. Method embodiments use previously acquired 3D images or images acquired using imaging modalities different than the one used to acquire the 2D image.

15 Claims, 2 Drawing Sheets

METHOD TO CORRECT THE REGISTRATION OF RADIOGRAPHY IMAGES

CROSS-REFERENCE TO RELATED APPLICATIONS

This application claims priority under 35 U.S.C. §119(a)-(d) of the filing date of prior-filed, co-pending French patent application serial number 0756592, filed on 19 Jul. 2007, which is hereby incorporated by reference in its entirety.

FIELD OF THE INVENTION

The field of the invention relates generally to medical imaging, and more particularly to radioscopy.

DESCRIPTION OF PRIOR ART

There are known X-ray systems comprising especially an X-ray tube, an X-ray detector, a table and a C-shaped arm which is generally a vascular C-arm. These systems are able to shift in all three dimensions of a space. This mobility enables a practitioner to acquire images for any part whatsoever of a patient's body lying on the table. In general, the table is capable of moving in all three possible translation motions associated with a given space, while the C-arm is capable of moving in three possible rotations associated with this space.

The practitioner uses an intervention radiology system to have tools such as a catheter or a coil within the patient's body, especially within the head. The geometry of the images acquired must be known with precision so as to help the practitioner position his tools.

Two types of image acquisition are possible with these systems. The practitioner can acquire 2D images obtained by projection of X-rays on the detector. Each image is obtained for a given position of the tube and of the detector. The part of the patient's body is then projected on the detector in a conical projection. To guide his tools during a procedure, the practitioner can use these images in two dimensions obtained with or without contrast medium. These images acquired with low doses of X-rays are called fluoroscopic images.

The practitioner can also acquire images in three dimensions. During the acquisition of these images, the tube and the detector move around the patient. Several images in projection are thus acquired by the C-arm and, from these images, the part of the body to be viewed can be rebuilt in three dimensions. The contrast of these images in three dimensions can be improved through the injection of a contrast medium.

The fluoroscopic images are acquired in real time while the 3D image, which is generally a pre-operation image, is static. To improve the tool-guiding system, there are known ways of projecting the 3D image on the fluoroscopic image. This method is called 3D enhanced fluoroscopy. It is also possible to project the 3D image on a pre-operational 2D image, for example a DSA image. In reverse, there are known ways of back-projecting the 2D image on a 3D image. This method is called 3D road mapping.

The difficulty of implementing these methods relates to the fusing of two images in taking account of the right geometry of acquisition of the system. Indeed, to project the 3D image on the 2D image or vice versa, the acquisition geometry of the medical system should be capable of being determined whatever the position of this system in space. The acquisition geometry of the system is relative to the positioning of the tube and of the detector in a given reference system. This acquisition geometry is defined both by the position in space of the C-arm and that by of the table relative to a given referential. The degrees of freedom of the table can be modeled without great difficulty using known models. The C-arm however is more difficult to model.

To model this C-arm, emphasis is placed on the computation of the projection matrices which make a point located in the 2D image correspond to a point located in the rebuilt 3D image. A pixel of the 2D image is supposed to correspond to a projection of a 2D voxel of the rebuilt 3D image on the X-ray detector inasmuch as this image would have been placed at the position of the body. A projection matrix should be capable of being produced for each position of the C-arm in space. This projection matrix is associated with the acquisition geometry of the system.

An example of the modeling of this C-arm is described in the document FR 2 879 433. The document FR 2 879 433 proposes a method in which the projection matrices are computed on the basis of a calibration of the position of the C-arm and of computations of a certain number of geometry parameters.

In this document, a projection matrix can be subdivided into two sets of geometrical parameters: intrinsic parameters and extrinsic parameters. The intrinsic parameters correspond to projection parameters of the X-ray tube on a projection image or more specifically to the X-ray detector. The extrinsic parameters correspond to a general position of the medical system defined by rotations and translation of this system in a given reference system.

This document makes it possible to determine the intrinsic and extrinsic parameters for an arbitrary orientation of the C-arm. These parameters enable the projection matrix to be forecast.

The document FR 2 879 433 conserves the simplicity of the rigid module while at the same time locally adjusting certain of its parameters so as to approach the real behavior of the C-arm. The method described makes it possible to determine a calibration matrix corresponding to a particular position of the C-arm called a calibration position.

This method is also used to apply a rigid transformation to this calibration matrix in order to obtain a projection matrix for any position whatsoever of the system in space. The rigid transformation corresponds to rotations and translations of the C-arm. This transformation is built on the basis of values of angles formed by the C-arm relative to the three axes and also generally on the basis of a distance between the tube and the detector. These values of angles and this distance are generally acquired by means of sensors of the medical system.

This mode of computation of the projection matrices enables an optimal theoretical registration between the fluoroscopic images and the pre-operational 3D image if it is assumed that the patient is not moving. This registration will hereinafter be called geometrical registration. However, in practice, it has been seen that said registration is not precise enough, especially in the following cases:

case 1: shifting of the table during a medical intervention, case 2: movement by the patient during a medical intervention, this movement possibly being for example respiratory motion, a motion of the body or of the head, case 3: deformation or motion of organs to be analyzed during the intervention phase, case 4: the 3D image used to perform the enhanced 3D fluoroscopy method is produced from a previous treatment, typically six months earlier, when this image is obtained according to other modalities of acquisition.

SUMMARY OF THE INVENTION

Embodiments of the invention aim to overcome theses and other drawbacks of the techniques explained above. To this end, an embodiment of the invention proposes a method for the correction of geometrical registration.

To do this, an embodiment of the invention comprises a correction algorithm capable of determining a residual transformation especially where the cases 1, 2, 3 and/or 4 occur during a medical intervention.

The correction algorithm of the invention comprises means to determine the residual transformation by comparing the pre-operational 3D image with a fluoroscopic image. This residual transformation is determined according to a registration based on the content of the image. The fluoroscopic image is acquired in a position of the C-arm and in a position of a patient which are positions used by the invention to execute the 3D enhanced fluoroscopic method.

Once the residual transformation is computed, it is combined with a geometrical registration. This geometrical registration is preferably the one proposed by the teaching of the document FR 2 879 433. Other existing types of geometrical registration may also be used.

With embodiments of the invention, whatever the position of the C-arm around the patient, it is not necessary to recompute the registration based on the content of the image as in the prior art. Indeed, the registration based on the content of the image makes it possible solely to initialize the parameters of the geometrical registration when one of the instances described here above takes place. Thus, whatever the position of the C-arm about the patient, only the geometrical registration is recomputed, enabling a gain in time and a reduction of the computation and memory resources.

In the prior art, the combination of the registration based on the content of the image with the geometrical registration is not natural. Indeed, the known and usual procedure is to use either one of these two types of image registration and not both types at the same time.

The use of geometrical registration in this combination enables the real-time performance of a registration comprising the movement of the C-arm without any additional registration. The use of the C-arm based on the content of the image makes it possible to refine the precision of the geometrical registration. The projection of the 3D image on the fluoroscopic image obtained according to the enhanced fluoroscopy method is consequently more rigorous. Thus, in the invention, the registration based on the content of the image is used in order to improve the geometrical registration.

In embodiments of the invention, the registration based on the content of the image is thus only a step of initialization of the geometrical registration. Any change in the geometry of the medical system induced by the motion of the C-arm is then recomputed in real time with the projection matrix.

Embodiments of the invention also make it possible to obtain real-time correction when the organs to be analyzed are rigid and/or non-rigid. This correction eliminates the deformation and/or the motion of the organs.

Embodiments of the invention also enable the use of the method of enhanced 3D fluoroscopy even with a 3D image that has been pre-acquired or acquired with other modalities.

The aim of an embodiment of the invention therefore is to set up the residual transformation to be applied to the 3D model in order to correct a projection matrix of the prior art.

An embodiment of the invention therefore pertains to a method for correcting registration of radiology images. The method includes emitting X-rays onto a body to project the X-rays with a given incidence on a detector of a medical system, wherein the X-rays are revealed by a projected 2D image having projection pixels;

acquiring a 3D image of the body using said medical system;

determining an acquisition geometry of the X-ray medical system by computing an initial projection matrix, performing a projection of the 3D image from the determined initial projection matrix;

making a registration based on a content of the image of the projection of the 3D image with the radiography image from the information contained in these images, computing a new projection matrix by combining the initial projection matrix with the registration based on the content of the 3D image; and projecting the 3D image on a radiography image as a function of the new projection matrix.

An embodiment of the invention also relates to an X-ray system for implementing said method for correcting registration of radiography images.

BRIEF DESCRIPTION OF THE DRAWINGS

Embodiments of the invention will be understood more clearly from the following description and the accompanying figures. These figures are given by way of an indication and in no way restrict the scope of the invention. Of these figures.

DETAILED DESCRIPTION OF THE INVENTION

Figure 1:
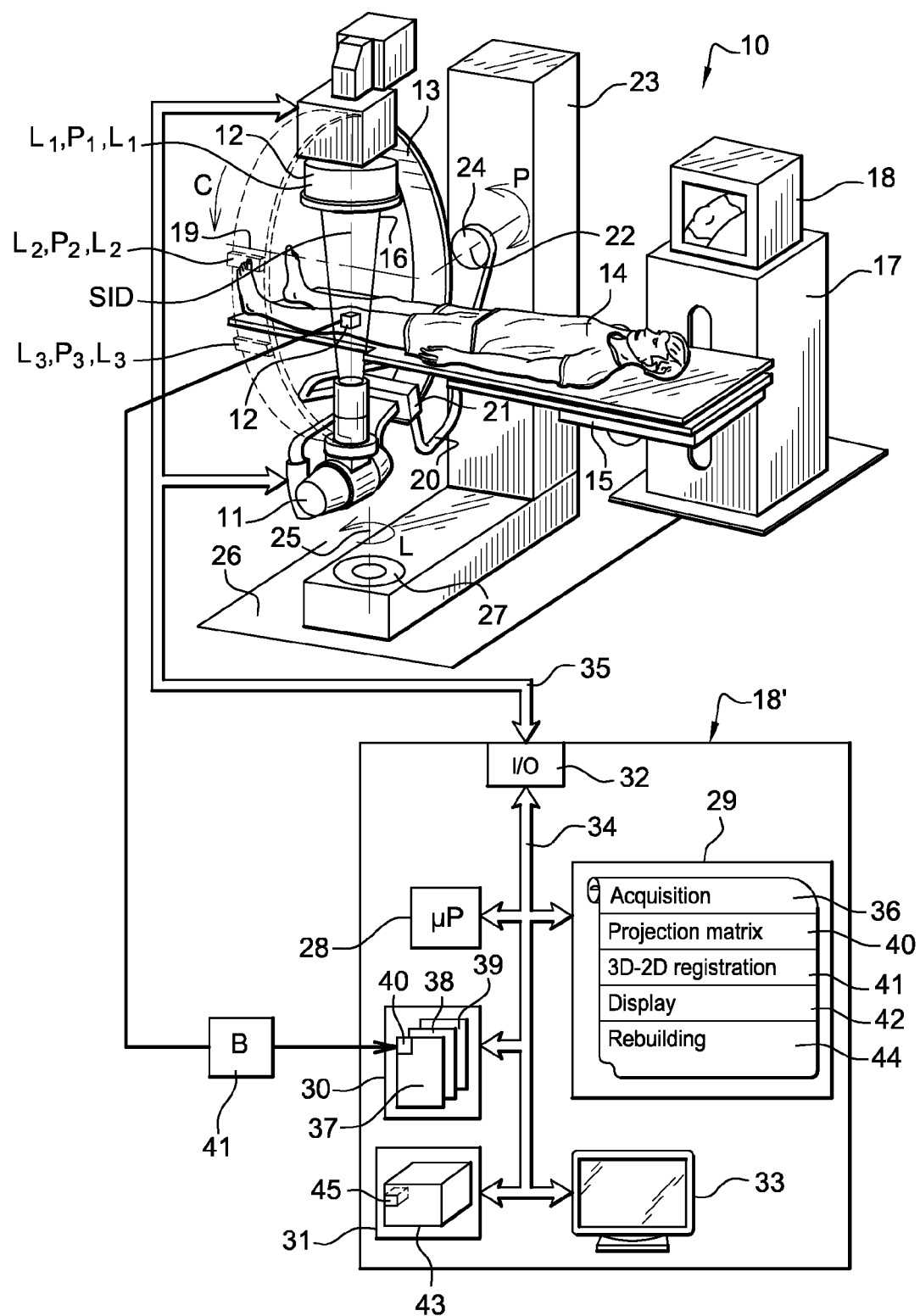
FIG. 1 is a schematic view of an X-ray system used with the method of the invention.

FIG. 1 shows a medical system 10 used with the method according to the invention. This medical system 10 can be especially a radiology or radioscopic system. This system 10 has an X-ray tube 11 and an X-ray detector 12 hooked to a C-shaped arm or C-arm 13. A patient 14 reclines on a table 15. This table 15 is positioned between the tube 11 and the detector 12. The detector 12 is positioned so that a main direction of emission of rays 16 is on the whole perpendicular to one face of the detector 12. The table 15 is connected to a base 17 on which a computer system 18 is laid. This computer system 18 enables especially the acquisition and display of 2D or 3D images.

More specifically, the C-arm 13 is capable of rotating about an axis 19. This axis 19 is perpendicular to a surface demarcated by the C-arm 13 and passes through the middle of a segment demarcated by the emitter 11 and the detector 12. For this purpose, the C-arm 13 is connected to an intermediate arm 20 by means of a sliding link 21. The intermediate arm 20 is capable of rotating about an axis 22 on the whole perpendicular to one face of an L-shaped support 23. To this end, the intermediate arm 20 is connected to the support 23 by means of a rotational link 24. The support 23 is capable of rotating about an axis 25 that is on the whole perpendicular to a ground 11. To this end, the support 23 is connected to the ground 25 by means of a rotating link 27.

The C-arm 13 is therefore capable of rotating about three axes 19, 22 and 25 which form a referential system. One position of the C-arm 13 may therefore be located in the referential system by three angles L, P and C that may be formed by this C-arm 13 respectively with the axes 19, 22 and 25 relative to a reference position. The position of the C-arm 13 is also defined by a distance SID between the tube 11 and the detector 12.

In one example of image acquisition using the X-ray system 10, the tube 11 and the detector 12 are situated on either side of the patient 14. The tube 11 is a conical X-ray source 15 which is projected on the detector 12. This detector 12 has sensors which measure the intensity of the rays that it receives. In general, the tube 11 is capable of rotating about the patient 14 along any direction whatsoever.

The computer system 18 comprises a control unit 18'. This control unit 18' has a microprocessor 28. This microprocessor 28 is connected to a program memory 29, data memories 30 and 31, an input/output interface 32 and a screen 33, by means of a communications bus 34. The input/output interface 32 emits output signals intended for the medical system 10 and receives input signals sent out by this medical system 10 by means of a communications bus 35.

When the microprocessor 28 executes an acquisition program 36, output signals may be sent so as to position the tube 11 in a particular position. Other output signals may also be sent to the tube 11 to control the emission of the X-rays. One or more 2D projection images 37-39 can then be acquired for different angles of incidence of X-rays. For example, 2D image acquisitions can be done for the positions of the C-arm referenced (L1, P1, C1)-(LN, PN, CAN). Information contents pertaining to the 2D images 37-39 are stored inside the memory 28. These information contents pertaining to the intensity of the X-rays received are associated with pixels 40 for the projection of the images 37-39.

The microprocessor 28 executes a program 40 for computation of the initial projection matrix. This projection matrix is computed from a modeling of the C-arm 13.

To model the motions of the C-arm 13 in a space, a model of the C-arm is used. In this model of the C-arm, it is possible to consider the C-arm 13 of the medical system 10 in an ideal way. This C-arm 13 is then rigid, the tube 11 and the projection 12 are attached rigidly to the C-arm 13 and motions of this C-arm 13 can be described by perfect rotations about three axes 19, 22 and 25. It is also assumed that internal parameters of the system pertaining especially to a positioning of the tube 11 and of the detector 12 are constant.

From a defined model of the C-arm 13, the microprocessor 28 computes the acquisition geometry of the system for an arbitrary position of this system defined by the parameters L, P and C. These parameters may be measured by means of position sensors (not shown) situated at the position of the mobile links 21, 24, 27. Electrical signals coming from the sensors can be sent to the computer system 18.

The program 40 thus enables the computation of the projection matrix associated with any unspecified position of acquisition of the system about the patient 14 as a function of the parameters L, P and C coming from the sensors of the medical system 10.

The microprocessor 28 executes a 3D-2D registration program 41 based on the content of the image. This 3D-2D registration based on the content of the image enables the alignment of a 2D image with a projection of a 3D image on the basis of the information contained by such images.

The microprocessor 28 executes a display program 42 which enables the display on the screen 33 of the result of the combination of the 3D images with the 2D images.

Figure 2:
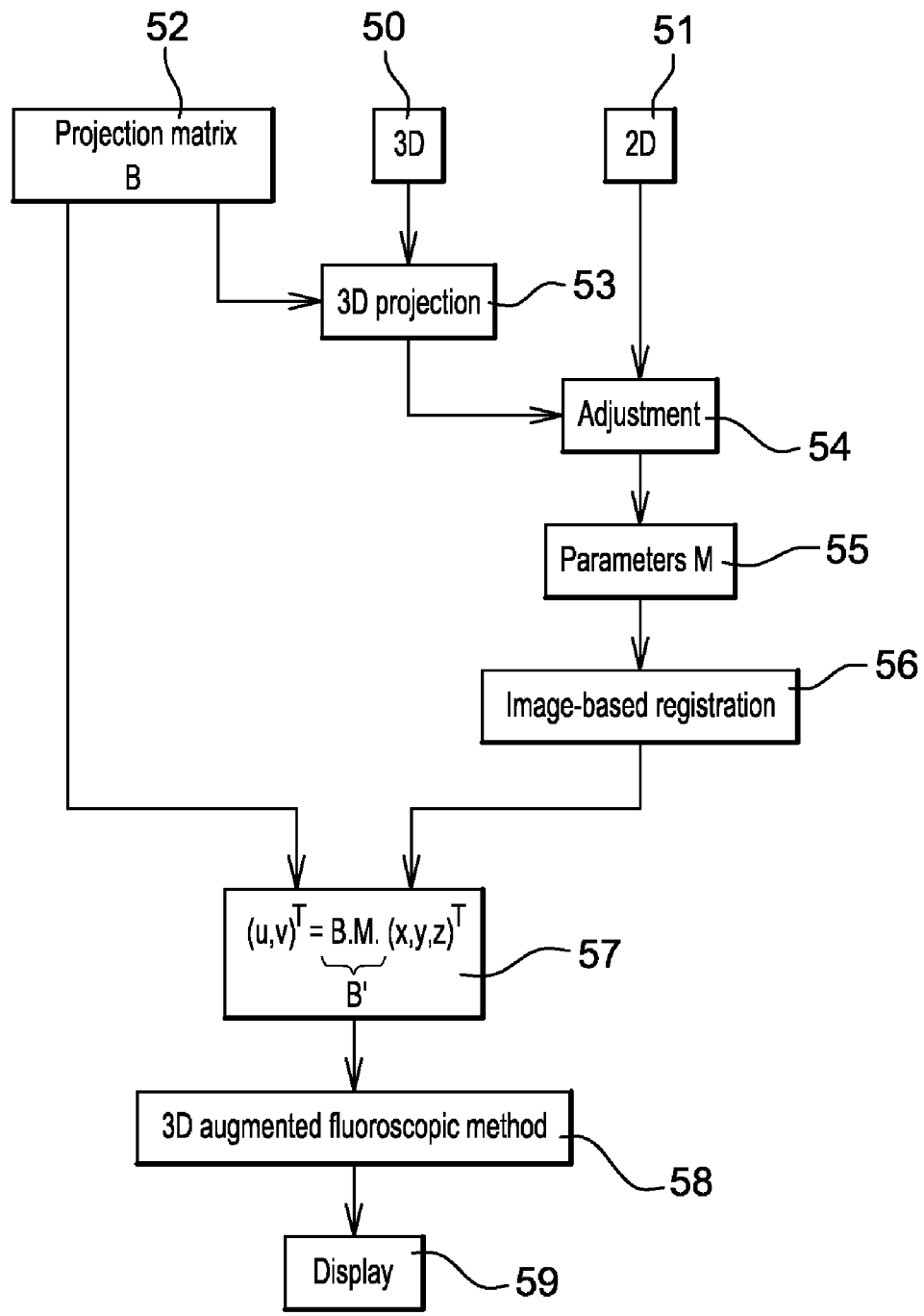
FIG. 2 is a schematic view of an implementation of the method.

FIG. 2 is a diagram of steps of the method of the invention. The method of the invention is applied in a preferred embodiment, as shown in FIG. 2, to the enhanced 3D fluoroscopy method.

At a step 50, a 3D image 43 is acquired. This image 43 is a pre-operation image. It can be obtained at the beginning of the medical operation. In this case, the image 43 is obtained by execution by the microprocessor 28 of a rebuilding program 44. To this end, from the 2D images, the program 44 rebuilds the final volume image 43. Information contents of this image 43 are stored at memory addresses of the memory 31. These information contents correspond to voxels 45 of the image 43.

This image 43 stored inside the memory 31 can be obtained before medical operation. In this case, it can be obtained by prior acquisition, typically an acquisition performed 6 months earlier. It can be obtained by means of any other acquisition system, for example, especially computer tomography, a radiography system taking 3D pictures by rotation, magnetic resonance (MR) systems, computerized positron emission tomography systems, ultrasound systems, nuclear medicine systems and 3D radiography systems.

At a step 51, radiography images are acquired. In the example of FIG. 2, these are 2D fluoroscopic images. These images are stored in the memory 30. These fluoroscopic images show the anatomical information and/or the guiding tools.

At a step 52, the initial projection matrix to be associated with any unspecified position of acquisition of the system about the patient 14 is determined. In a preferred embodiment, this initial projection matrix 41 is preferably determined according to the teaching of the document FR 2 879 433.

The initial matrix B of projection 41 is associated with each position (L1, P1, C1)-(LN, PN, CN) for the acquisition of the C-arm 13. This initial projection matrix 41 obtains correspondence between a point 42 of the patient 14 and an information content assigned to projection pixels 40 in a 2D image acquired for a given position of the C-arm 13.

More specifically, the initial projection matrix 41 may be subdivided into two sets of geometrical parameters: intrinsic parameters and extrinsic parameters.

The intrinsic parameters correspond to projection parameters of the X-ray tube 11 on a projection image or, more specifically, on the X-ray detector 12. The extrinsic parameters correspond to a general position of the medical system defined by rotations and translations of the system in a given referential system.

In a preferred embodiment, the initial projection matrix is produced for a given position of the C-arm 13 by means of a limited number of pre-computed projection matrices called calibration matrices. These calibration matrices are computed for particular positions of the system called calibration positions. In general, at least one calibration matrix is computed. In one example, certain of the acquisition positions (L1, P1, C1)-(LN, PN, CN) are calibration positions. In one example, between 10 and 30 calibration positions are determined. Each calibration position may have several calibration matrices corresponding to it. In another example, between 10 and 30 calibration matrices are pre-computed.

There are known ways of determining the calibration matrices by having available an element of a known shape called a ghost on the table 15. In one mode of implementation, the ghost is formed by beads whose conformation in space is known with precision. After the ghost has been positioned, X-rays are projected with a given incidence on the detector 12 and are revealed by one of the 2D projected images 37-39 with projection pixels 40. Then, the calibration matrix which makes one point of the ghost correspond with an information content allocated to projection pixels is computed.

Then, for any acquisition position whatsoever of the medical system 10, it is possible to predict the corresponding initial projection matrix B. To predict any initial projection matrix B whatsoever, the parameters of the calibration matrices and/or corresponding geometrical parameters are interpolated between the calibration positions.

At a step 53, a projection of the volume image 43 is made. This projection of the image 43 is made by means of the initial projection matrix obtained at the step 52. The initial projection matrix is computed for the position of the fluoroscopic image acquisition system 10.

At the step 54, an initialization step is done before the application of the registration based on the content of the image. This initialization step is an adjustment between the fluoroscopic image and the 3D projection image. This initialization step is necessary should there be a major movement of the patient and/or of the table between the acquisition of the fluoroscopic image and the acquisition of the 3D image. This adjustment may be done manually and visually by the practitioner. In this case, the practitioner shifts the table and/or the 3D image. This shift makes it possible to obtain visually the best adjustment between the 2D image and the projection of the image 43.

In practice, this initialization step is not necessary for small movements by the patient.

After this initialization step, the 3D/2D registration based on the content of the image of the step 56 is done between the projection of the 3D image and the fluoroscopic 2D image. The registration based on the content of the image of the step 56 is done on the basis of the information contained in the images. This registration is obtained according to a rigid transformation of parameters M. These parameters M are determined in the step 55.

The rigid transformation of the parameters M corresponds to rotations and/or to translations forming the parameters. These parameters are different depending on the cases 1, 2, 3 or 4 that occur.

In the case of pure translation of the table, namely the case 1, during the medical operation, the parameters M are three in number. They consist of a 3D translation.

In the case of a motion of the patient 14, namely the case 2, or when the 3D image comes from a previous acquisition or from another modality, namely case 4, the parameters M are six in number. They are formed by a 3D rotation and a 3D translation.

When there is only one motion of the organ to be analyzed, namely in the case 3, the shifting of the organ can be mobilized by motions of translations and rotations. In the case of a deformation of the organs, namely case 3, the deformation can be modeled by a large family of existing functions, especially the similitude function and the parametric function.

In practice, to perform the registration based on the content of the image, the 3D image is iteratively positioned and oriented until the measurement of a similarity score between the 3D and 2D images is optimal. The similarity score may be determined according to two known criteria of similarity. These criteria may be the primitive-based criteria and/or the iconic criteria.

In the iconic approaches, the fluoroscopic image is compared to a synthetic image generated from the 3D image and the current estimation of the parameters of the transformation.

In the primitive-based criteria, primitives are extracted both from the 3D image and from the fluoroscopic image. These extracted primitives are used to compute the similarity score. In vascular imaging, it is typically the central lines of the vessels that are used.

In one variant, when the cases 1 and 2 occur, the registration based on the content of the image may be executed with additional external sensors placed on the patient's head and/or on the table. These sensors may be magnetic probes based on optical or electromagnetic technologies.

The registration based on the content of the image should not be redone permanently. It is enough to do it once for an angulation of the C-arm.

Once the rigid transformation of the parameters M is known, the initial projection matrix of the step 52 is used in real time to foresee the changing of the acquisition geometry induced by the motion of the C-arm. Such an approach enables execution of the enhanced fluoroscopy method even if the C-arm 13 is shifted. With the invention, the enhanced fluoroscopy method is performed without any additional registration.

Thus, once the rigid transformation of parameters M is known, said transformation is applied, in the step 57, to the initial projection matrix of the step 52. A new projection matrix $B_i'$ is determined at the step 57, i being a position of the C-arm about the patient. This new projection matrix $B_i'$ is a combination of the rigid transformation of parameters M and of the initial projection matrix $B_i$ of the step 52. This combination enables the correction, from the registration based on the image content, of a residual registration of the projection matrix when especially the cases 1 and/or 2 and/or 3 and/or 4 occur.

The new projection matrix $B_i'$ enables a registration capable of setting up a precise correspondence of a voxel (X, Y, Z) of the 3D image at a point (u, v) of the fluoroscopic image.

This correspondence may be provided by the following equation:

$$(u,v)^T = B_i' * M * (X,Y,Z)^T$$

with the projection matrix:

$$B_i = I_i * E_i$$

where I represents the intrinsic parameters and E the extrinsic parameters and the index i corresponds to a given position of the C-arm 13. The new projection matrix $B_i'$ is equal to:

$$B_i' = B_i * M$$

This new projection matrix B' makes it possible to obtain a valid 2D projection of the 3D point $(X, Y, Z)^T$.

At a step 58, a projection of the 3D image on the fluoroscopic image is performed with precise registration, according to the 3D enhanced fluoroscopic method. The step 58 provides a registration image at output, enabling the practitioner to view both the intervention tool and the anatomy at the same time. At the step 59, the registration image is displayed on the screen 33.

If the cases 1 and 2 occur during the medical intervention, a new fluoroscopic image is acquired and the rigid transformation of parameters M is recomputed.

In the case of the medical applications on rigid organs, namely an operation performed in the vertebral column or an intercranial operation, the adjustment step 54 is preferably done only when the patient and/or the table are shifted between the acquisition of the 3D image and the acquisition of the fluoroscopic image.

In the case of medical applications to non-rigid organs, for example an embolism of the liver or a heart operation, the rigid transformation of parameters M is used to perform a real-time correction of the method of enhanced fluoroscopy in order to compensate for the deformation and/or the motion of the organs.

If the 3D image used by the enhanced 3D fluoroscopy method is derived from a previous acquisition or from another modality, namely case 4, a rigid transformation of initialization is computed before the medical operation. This rigid transformation of initialization is used, before the application of the method of FIG. 2, to register this 3D image on the fluoroscopic image. Thus, if the 3D image comes from another modality and/or a previous acquisition, an initial registration is done in comparing the previous 3D image with an acquired 3D image and/or in performing an image-based 3D-2D registration.

What is claimed is:

1. A method for correcting registration of radiology images, the method comprising:
   acquiring a 3D image of body using a medical imaging system;
   acquiring a 2D image of the body using an X-ray medical imaging system;
   determining an acquisition geometry of the X-ray medical system during the acquiring of the 2D image by computing an initial projection matrix;
   projecting the 3D image of the body with the determined initial projection matrix, making a 2D projection of the 3D image;
   registering the 2D projection of the 3D image with the acquired 2D image;
   computing a new projection matrix by combining based on the registration of the 2D projection of the 3D image and the acquired 2D image; and
   projecting the acquired 3D image on the acquired 2D image with the new projection matrix.

2. The method of claim 1, further comprising:
   displaying the projected acquired 3D image on the acquired 2D image.

3. The method of claim 1, further comprising:
   acquiring the 3D image at a start of a medical intervention or during a previous treatment.

4. The method of claim 1, further comprising:
   acquiring the 3D image using an imaging modality different than used in the acquiring the 2D image,
   wherein the imagine modality used to acquire the 3D image is one of a computer tomography system, a magnetic resonance (MR) system, a computerized positron emission tomography (PET) system, an ultrasound system, a nuclear medicine system, or a 3D radiography system.

5. The method of claim 1, wherein determining of the initial projection matrix comprises:
   determining a model of a C-arm of the medical imaging system from several projection matrices called calibration matrices; and
   computing the initial projection matrix for any position of the C-arm from the calibration matrices and from data given by one or more sensors.

6. The method of claim 5, further comprising:
   pre-computing each of the calibration matrices, wherein the pre-computing comprises:
   placing a phantom for which conformation is space is known with precision on a table;
   emitting X-rays to project with a given incidence on a detector of the system, wherein the X-rays are revealed by a projected 2D image having projection pixels,
   reading the 2D image radiographically to obtain the radiography image,
   and
   computing a calibration matrix that makes an information content assigned to projection pixels correspond to a point of the phantom.

7. Method according to claim 5, wherein computing the initial projection matrix for any position of the C-arm, further comprises:
   computing parameters of at least one of the calibration matrices or corresponding geometrical matrices.

8. The method of claim 3, wherein the registering the 2D projection of the 3D image with the acquired 2D image is an image-based 3D-2D registration.

9. The method of claim 8, wherein the image-based 3D-2D registration is a rigid transformation of parameters M in which:
   the 3D image is positioned iteratively, and
   said image is oriented until a measurement of a similarity score between the 3D image and the projection image is optimal.

10. The method of claim 9, wherein the measurement of a similarity score comprises:
    generating a synthetic image from the 3D image; and
    comparing the synthetic image with the radiography image as a function of an estimation of the parameters of the transformation.

11. The method of claim 10, wherein the measurement of the similarity score comprises:
    extracting primitives, in particular central lines of the vessels, both in the 3D image and in the radiography image.

12. The method of claim 3, wherein the registering the 2D projection of the 3D image with the acquired 2D image is done with at least one of additional external sensors placed on a patient's head or on a table that supports the patient, when at least one of the table or the patient are in motion during the medical intervention.

13. The method of claim 9, further comprising:
    acquiring a new radiography image and recomputing the rigid transformation of parameters M when at least one of a table or a patient are in motion during the medical intervention.

14. The method of claim 9, wherein, during a medical intervention on non-rigid organs such as the liver or the heart, the rigid transformation of parameters M is used to make a real-time correction of the projection of the acquired 3D image on the acquired 2D image in order to compensate for at least one of deformation or motion of the organs.

15. The method of claim 3, further comprising:
    computing a rigid transformation of initialization before the medical intervention.

* * * * *